United States Patent [19]

Van Rheenen

[11] 4,061,657
[45] Dec. 6, 1977

[54] PROCESS FOR PREPARING A 2(R) OR 2(S) TRICYCLIC LACTONE GLYCOL

[75] Inventor: Verlan H. Van Rheenen, Portage, Mich.

[73] Assignee: The Upjohn Company, Kalamazoo, Mich.

[21] Appl. No.: 725,866

[22] Filed: Sept. 23, 1976

Related U.S. Application Data

[60] Continuation of Ser. No. 575,526, May 8, 1975, abandoned, which is a division of Ser. No. 374,348, June 28, 1973, abandoned.

[51] Int. Cl.$^2$ .............................................. C07D 307/93
[52] U.S. Cl. .................................................. 260/343.3 P
[58] Field of Search .................................... 260/343.3 P

[56] References Cited

U.S. PATENT DOCUMENTS

| 3,816,460 | 6/1974 | Kelly | 260/343.3 P |
| 3,904,648 | 9/1975 | Kelly | 260/343.3 P |
| 3,953,473 | 4/1976 | Van Rheenen | 260/343.3 P |

Primary Examiner—Natalie Trousof
Assistant Examiner—Jane T. Fan
Attorney, Agent, or Firm—Robert A. Armitage

[57] ABSTRACT

A process for preparing optically active 2(S) or 2(R) tricyclic lactone glycols of the formula

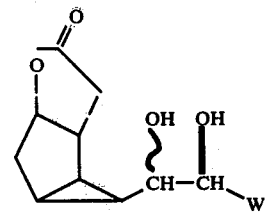

or

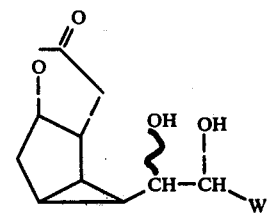

wherein W is 1-pentyl, 1-pent-cis-2-enyl, or 1-pent-2-ynyl. This process is useful for preparing stereospecifically prostaglandins having pharmacological utility.

6 Claims, No Drawings

PROCESS FOR PREPARING A 2(R) OR 2(S) TRICYCLIC LACTONE GLYCOL

The present application is a continuation of Ser. No. 575,526, filed May 8, 1975, now abandoned, which application was a division of Ser. No. 374,348, filed June 28, 1973, now abandoned. A further continuation application of Ser. No. 374,348 has now issued as U.S. Pat. No. 3,953,473 on Apr. 27, 1976.

The present invention relates to a process for the preparation of tricyclic lactone glycol intermediates which are useful compounds in the synthesis of prostaglandins. The essential material constituting a disclosure of the present invention is incorporated here by reference from U.S. Pat. No. 3,953,473, issued Apr. 27, 1976.

I claim:

1. A process for preparing an optically active 2S tricyclic lactone glycol of the formula

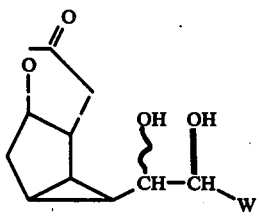

or a racemic compound of that formula and the mirror image of that formula, wherein W is 1-pentyl, cis 1-pent-2-enyl, or 1-pent-2-ynyl, and ∼ indicates attachment of the hydroxyl to the side chain in alpha or beta configuration, which comprises starting with an optically active 2R tricyclic lactone glycol of the formula

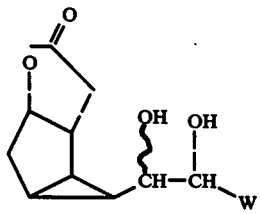

or a racemic compound of that formula and the mirror image of that formula, wherein W and ∼ are as defined above, and subjecting said 2R glycol successively to the following reactions:

a. monosulfonation to replace the hydrogen of the C-2 hydroxyl with a sulfonyl group of the formula —$SO_2$—$R_3$ wherein $R_3$ is alkyl of one to 10 carbon atoms, inclusive, aralkyl of 7 to 12 carbon atoms, inclusive, phenyl or phenyl substituted with one or 2 halo or alkyl groups of one to 4 carbon atoms, inclusive:

b. acylation to replace the hydrogen of the C-1 hydroxyl with an acyl group of the formula —C(O)—$R_4$ wherein $R_4$ is alkyl of one to 10 carbon atoms, inclusive, aralkyl of 7 to 12 carbon atoms, inclusive, phenyl or phenyl substituted with one or 2 halo or alkyl groups of one to 4 carbon atoms, inclusive;

c. transformation of the product of step b to an optically active 2 S compound of the formula

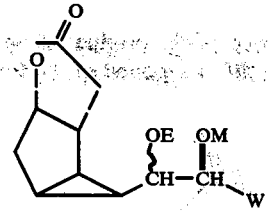

or a racemic compound of that formula and the mirror image of that formula, wherein one of E and M is hydrogen and the other is an acyl group of the formula —C(O)$R_4$ wherein $R_4$ is as defined above, wherein ∼ indicates attachment of the moiety to the side chain in either alpha or beta configuration, and wherein W is as defined above; and d. replacement of the acyl group —C(O)$R_4$ with hydrogen.

2. A process according to claim 1 wherein $R_3$ is p-tolyl and $R_4$ is methyl.

3. A process according to claim 2 wherein W is 1-pentyl.

4. A process preparing an optically active 2R tricyclic lactone glycol of the formula

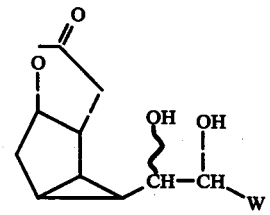

or a racemic compound of that formula and the mirror image of that formula, wherein W is 1-pentyl, cis 1-pent-2-enyl, or 1-pent-2-ynyl, and ∼ indicates attachment of the hydroxyl to the side chain in alpha or beta configuration, which comprises starting with an optically active 2S tricyclic lactone glycol of the formula

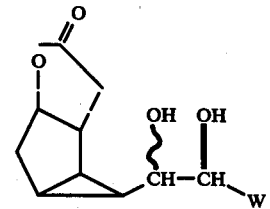

or a racemic compound of that formula and the mirror image of that formula, wherein W and ∼ are as defined above, and subjecting said 2S glycol successively to the following reactions:

a. monosulfonation to replace the hydrogen of the C-2 hydroxyl with a sulfonyl group of the formula —$SO_2$—$R_3$ wherein $R_3$ is alkyl of one to 10 carbon atoms, inclusive, aralkyl of 7 to 12 carbon atoms, inclusive, phenyl or phenyl substituted with one or 2 halo or alkyl groups of one to 4 carbon atoms, inclusive:

b. acylation to replace the hydrogen of the C-1 hydroxyl with an acyl group of the formula —C(O)—$R_4$ wherein $R_4$ is alkyl of one to 10 carbon atoms, inclusive, aralkyl of 7 to 12 carbon atoms, inclusive, phenyl or phenyl substituted with one or 2 halo or alkyl groups of one to 4 carbon atoms, inclusive;

c. transformation of the product of step *b* to an optically active 2R compound of the formula

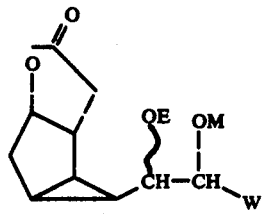

or a racemic compound of that formula and the mirror image of that formula, wherein one of E and M is hydrogen and the other is an acyl group of the formula —C(O)R$_4$ is as defined above, wherein ~ indicates attachment of the moiety to the side chain in either alpha or beta configuration, and wherein W is as defined above; and d. replacement of the acyl group —C(O)R$_4$ with hydrogen.

5. A process according to claim 4 wherein R$_4$ is p-tolyl and R$_4$ is methyl.

6. A process according to claim 5 wherein W is 1-pentyl.

* * * * *